United States Patent [19]

Hanyuda et al.

[11] 3,933,857
[45] Jan. 20, 1976

[54] POLYMERIZABLE CYCLOACETAL RESINOUS COMPOSITION

[75] Inventors: Toshiaki Hanyuda, Yokohama; Eiichiro Takiyama, Tokyo, both of Japan

[73] Assignee: Showa Highpolymer Co., Ltd., Japan

[22] Filed: Oct. 18, 1973

[21] Appl. No.: 407,626

[52] U.S. Cl..... 260/340.7; 204/159.22; 260/86.1 R; 260/86.3; 260/86.7; 260/88.3 A; 260/836; 260/867
[51] Int. Cl.² ................ C07D 317/04; C08F 24/00
[58] Field of Search ...... 260/836, 867, 862, 88.3 A, 260/86.1 E, 340.7

[56] References Cited
UNITED STATES PATENTS

| | | | |
|---|---|---|---|
| 2,687,407 | 8/1954 | Orth | 260/88.3 |
| 2,975,156 | 3/1961 | Fekete | 260/67 |
| 3,087,918 | 4/1963 | Guest et al. | 260/88.3 |
| 3,247,282 | 4/1966 | Englisch et al. | 260/827 |
| 3,291,860 | 12/1966 | Nordstrom | 260/866 |
| 3,296,337 | 1/1967 | Zimmermann | 260/867 |
| 3,468,857 | 9/1969 | Graver et al. | 260/80.3 |

FOREIGN PATENTS OR APPLICATIONS

| | | | |
|---|---|---|---|
| 757,573 | 9/1956 | United Kingdom | 260/867 |

*Primary Examiner*—Donald E. Czaja
*Assistant Examiner*—E. A. Nielsen
*Attorney, Agent, or Firm*—Wenderoth, Lind & Ponack

[57] ABSTRACT

This invention relates to a polymerizable cycloacetal resinous composition, characterized by reacting 1 equivalent of diallylidenepentaerythritol (I) with 0.8 – 2.0 equivalents of polyhydric alcohol-unsaturated monocarboxylic acid ester mono-ol (II) having both a hydroxyl group and a polymerizable or copolymerizable unsaturated bond in the same molecule, with or without a solvent, in the presence of a polymerization inhibitor and addition reaction catalyst.

2 Claims, No Drawings

POLYMERIZABLE CYCLOACETAL RESINOUS COMPOSITION

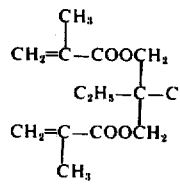
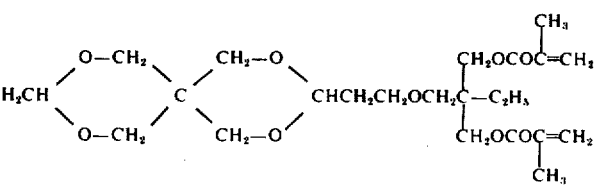

This invention relates to a polymerizable cycloacetal resinous composition prepared by reacting unsaturated cycloacetal compound with unsaturated alcohol having both a polymerizable or copolymerizable unsaturated bond and hydroxyl group in the same molecule.

Cycloacetal compound prepared by the condensation of a polyhydric alcohol such as pentaerythritol and sorbitol with unsaturated aldehyde such as crotonaldehyde and acrolein is well known as a spiroacetal resin. Among them, diallylidenepentaerythritol prepared by the condensation of pentaerythritol with acrolein and triallylidenesorbitol prepared by the condensation of sorbitol with acrolein are valuable since a double bond in their structure has special reactivity, and it is well known that they react with active hydrogens of polycarboxylic acids, polyhydric alcohols, or polythiols phenols to produce thermoplastic or thermosetting resins.

However, these double bonds are not always satisfactory in radical polymerizability, and the reactivity with the hydrogen of an active amine is not satisfactory. Consequently, this lessens their utility.

We have studied the various properties of these cycloacetal groups, and found that they can be modified to have satisfactory radical polymerizability without damaging their essential features. We noticed that these double bonds react well with alcoholic hydroxyl groups without coloration, and that unsaturated bonds in acrylyl or methacylyl groups polymerize or copolymerize well with the same kinds or different kinds of polymerizable monomers. This was proven by the fact that the reaction of the above cycloacetal compound with a glycol unsaturated monocarboxylic acid ester e.g. hydroxylethylmethacrylate which is a monomer having both a hydroxyl group and unsaturated bond in the same molecule, trimethylolpropanedimethacrylate or glycerinedimethacrylate, provides an addition monomer which comprises substantially both of the above compounds. In the above reaction, addition reaction is completed without producing substitution reaction products and any other by-products, and accordingly the reaction can easily be carried out in a simple and inexpensive apparatus. A novel polymerizable cycloacetal addition product prepared by reacting diallylidenepentaerythritol with hydroxylethylmethacrylate in accordance with the present invention is represented by the following chemical formula.

In addition to diallylidenepentaerithritol, the other examples of polycycloacetal compound (I) which can be used in the present invention include polycrotonaldehyde acetal, polyacrolein acetal and the like, and they are synthesized by the method disclosed in Schulz "Angew, Chem." (vol. 62, No. 5, pp. 105-118, 1950). However, polyacrolein acetal is preferable in order to obtain a desired product having a light color by reacting with a polymerizable alcohol source as disclosed below.

Examples of glycol unsaturated monocarboxylic acid monoesters or polyhydric alcohol unsaturated monocarboxylic acid ester mono-ols (II) which react with polycycloacetal compound (I) include hydroxylethyl (or propyl) methacrylate, hydroxylethyl (or propyl) acrylate, hydroxylethyl (or propyl) crotonate, trimethylolpropanedimethacrylate, trimethylolpropanediacrylate, trimethylolethanedimethacrylate, trimethylolethanediacrylate, glycerinedimethacrylate and the like. They must have at least one alcoholic hydroxyl group and at least one unsaturated bond such as methacrylyl, acrylyl and crotonyl groups. Taking radical polymerizability and curing properties into consideration, a compound having methacrylyl group is generally preferable. However, when a soft curing product is desired or a reactivity with active amine hydrogen is desired, a compound having an acrylyl group is convenient.

According to the present invention, a novel cycloacetal resinous composition is prepared by reacting polycycloacetal compound (I) with a glycol unsaturated monocarboxylic acid monoester or polyhydric alcohol unsaturated monocarboxylic acid ester mono-ol (II) in an equivalent ratio of an acetal group (I) to (II) e.g. 1 to 0.8-2. 1-1.5 equivalents of (II) is sufficient for this reaction, but it is generally convenient to use an excess of (II) in order to improve the rate of this addition reaction. After the reaction is completed, the excess amount of component (II) may be removed, but the removement of the excess amount of component (II) depends on the use of the reaction product and is not always necessary. The rate of the reaction between the two components (I) and (II) is preferably more than 80 percent. If the reaction rate is below this value, the curing of the product sometimes is poor. Therefore, for general purpose, the component (II) should be used in an equivalent or excess amount to complete the reaction. The reaction between the two components (I) and (II) smoothly takes place without using solvent,

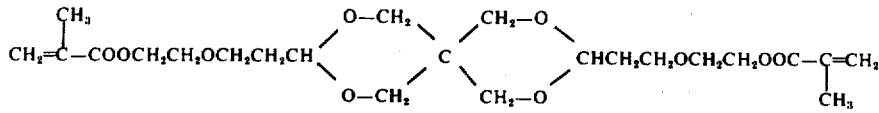

Further, a novel polymerizable cycloacetal addition product prepared by reacting diallylidenepentaerythritol with trimethylolpropanedimethacrylate is represented by the following chemical formula.

and accordingly it is economically advantageous to run the reaction without using a solvent. However, it may be convenient to perform the reaction in the presence of solvent for a paint and to use the reaction product as a paint as is. During the reaction between components (I) and (II), there is a possibility that a gelation may take place. Thus, it is preferable to perform the reaction in atmosphere of inert gas than in the air. However, such gelation can be prevented if a polymerization inhibitor such as hydroquinone, benzoquinone or the like is used. The inhibitor is used in an amount of 0.001–0.1 weight part per 100 weight parts of the total reactants. In order to accelerate the reaction, a small amount of acidic catalyst is required, and a suitable acidic catalyst employed for this purpose includes paratoluene sulfonic acid, diethylsulfuric acid, ethylsulfonic acid, BF$_3$-ether complex and the like. Among these catalysts, paratoluene sulfonic acid is inexpensive and satisfactory. The amount of the catalyst used is 0.1–1.0 weight part per 100 weight parts of the total reactants. If the amount of the catalyst used is less than the above value, the reaction takes much longer and this is economically undesirable. On the other hand, if the amount of the catalyst is more than the above value, there is a possibility that coloration or side-reactions take place. From this point of view, a generally preferable amount of catalyst is 0.2–0.4 weight part. The reaction temperature may be selected from within the range of 50° to 120°C, but the preferable reaction temperature range is from 60° to 20 C for the purpose of preventing coloration or unfavorable side-reaction. In order to obtain a reaction yield of more than 80 percent at 80°C, the reaction takes 12 to 15 hours.

The reaction product obtained by the present invention, for example cycloacetaletherpoly(meta)acrylate is very useful as a starting material for synthetic resin or modifier. The viscosity of the reaction product of this invention is generally several poises (1 to 10 poises) at room temperature without being diluted with other polymerizable monomers, and the reaction product contains polyfunctional monomers as a main component. Moreover, this reaction product is easily polymerized and cured by the action of a commonly available radical generator such as benzoylperoxide and the like. This is a significant property since commonly available polyesters must be diluted with polymerizable monomers such as styrene in order to obtain a viscosity of approximately several poises. The same situation applies to epoxyacrylics. Consequently, the shrinkage ratio of curing of commonly available starting materials is larger than that of the reaction product of this invention. This property makes the product of this invention useful as a starting material for FRP (fiber glass reinforced plastics), adhesives, casting materials, paints and the like. Moreover, the resinous product of this invention has excellent weather resistance and chemical resistance due to the acetal structure contained therein. Further, any kind of polymerizable monomers such as acrylic type monomers as well as styrene type monomers can be used as a diluent, and the cured product of this invention retains exellent tenacity, weather resistance and chemical resistance regardless of such diluent. Thus, the product of this invention having the above-mentioned various excellent properties may be used as a modifier for commonly available unsaturated polyester resins or epoxyacrylic type resins, and may be used for producing paints and adhesive by dissolving optional polymers. Also, the cycloacetal ether methacrylate of this invention may be used as an anaerobic one-package type adhesive in the same manner as polyethyleneglycol dimethacrylate, and the former is superior in weather resistance, thermal resistance and chemical resistance than the latter. The product of this invention may also be used as a polymerization plasticizer for vinyl chloride in the same manner as polyethyleneglycol dimethacrylate, and it was proven that the former is superior in weather resistance and compatibility to the latter. Thus, the product of this invention has various uses since it has a cycloacetal structure and low viscosity suitable for polymerization.

This invention is illustrated by the following examples, but is not restricted thereto.

EXAMPLE 1

260 weight parts of hydroxylethylmethacrylate (made by Mitsubishi Rayon Co.), 212 weight part of diallylidenepentaerythritol (made by Daicel Co.), 1.5 weight parts of para-toluenesulfonic acid and 0.25 weight part of hydroquinone were placed in a one liter-three necked flask equipped with a condenser, stirrer, theromometer and inlet tube for nitrogen. The mixture in the flask was stirred in the atmosphere of nitrogen, and reacted at a temperature of 80°–85°C for 10 hours. It was proven by infrared ray absorption spectrum determination that more than 80 percent of the reactants were reacted to produce a light yellowish resin having a low viscosity of 1.6–1.7 poises at 27°C. The reaction product had the following chemical formula:

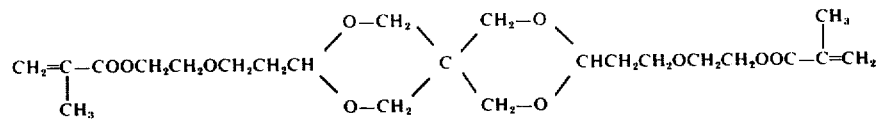

The thus obtained reaction product was easily cured in the presence of benzoylperoxide and dimethylaniline to form a transparent product having tenacity.

Both the reaction product diluted with 40 percent of styrene and the reaction product diluted with 40 percent of methylmethacrylate were also easily cured in the presence of benzoylperoxide and dimethylaniline to form a transparent hard product.

EXAMPLE 2

235 weight parts of hydroxylethylacrylate (made in Nagase Sangyo Co.), 200 weight parts of diallylidenepentaerythritol (made by Daicel Co.), 1.2 weight parts of para-toluenesulfonic acid and 0.2 weight part of hydroquinone were placed in the same type of flask as used in Example 1, and reacted at a temperature of 90°–92°C for 12 hours. It was proven by infrared ray absorption spectrum determination that 85 percent of the reactants were reacted. The thus obtained resin had a very light color and low viscosity (2.0 poises at 25°C), and the reaction product diluted with styrene or methylmethacrylate was cured in the presence of benzoyl peroxide to form a soft cured product.

EXAMPLE 3

400 weight parts of hydroxylethylacrylate, 212 weight parts of diallylidenepentaerythritol, 0.15 weight part of para-toluenesulfonic acid and 0.3 weight part of benzoquinone were placed in the same type of flask as used in Example 1, and reacted at 90°C for 15 hours. The thus obtained resinous composition had a viscosity of 1.2 poises at 25°C. After the reaction, the reaction mixture was neutralized with KOH-methanol solution, and to the reaction product were added 2 weight % of cumenehydroperoxide, 600 ppm of 1,4-benzoquinone and 0.2 weight % of dimethylaniline, thereby producing an anaerobic resinous composition having satisfactory preservability.

EXAMPLE 4

212 weight parts of diallylidenepentaerythritol, 560 weight parts of trimethylolpropanedimethacrylate composition, 2.5 weight parts of para-toluenesulfonic acid and 0.5 weight part of hydroquinone were placed in the same type of flask as used in Example 1, and reacted in the atmosphere of nitrogen at 80°C for 15 hours. It was proven by infrared ray absorption spectrum determination that approximately 90 percent of the reactants were reacted, and the thus obtained resin had a low viscosity (2.5 poises at 25°C). This resin was cured in the presence of benzoyl peroxide and dimethylaniline to form a transparent product having an excellent thermal resistance. This resin diluted with 60% of styrene or 20% of methylmethacrylate was cured in the same manner.

The following Examples 5 to 8 illustrate that a polymerizable cycloacetal compound of this invention may be used in connection with other unsaturated polyesters and thermoplastic resins. In these examples, there was used a cycloacetal compound prepared in Example 1 having the following chemical formula, Suitably the other cycloacetal compounds may also be used.

EXAMPLE 5

Preparation of Unsaturated Polyester (A)

Unsaturated polyester (A) was prepared by dissolving unsaturated alkyd of an acid value of 33.4 comprising 10.5 moles of propyleneglycol, 5 moles of maleic anhydride and 5 moles of phthalic anhydride, in 35% of styrene containing 0.02% of hydroquinone.

The polymerizable cycloacetal compound of this invention was mixed with the above prepared unsaturated polyester (A) in an optional ratio. To 100 weight parts of this mixture were added 1.5 weight parts of methylethylketoneperoxide and 0.8 weight part of cobalt naphthenate (6% Co), and the resultant composition was coated by a knife coater on a steel plate as used for testing a paint so as to make a thickness of a coated film 0.2 mm. As seen from Table 1, the copolymerizable cycloacetal compound of this invention proved to be very useful as a curing accelerator or a modifier for improving a surface drying property of the unsaturated polyester (A).

Table 1

| Composition of resin | pot life at 25°C (min.) | gelling time of coated film at 25°C (min.) | drying time (min.) | Sword hardness after 48 hours |
|---|---|---|---|---|
| unsaturated polyester (A) | 18 | 60 | not dried and remained sticky | unmeasurable |
| unsaturated polyester (A)80% polymerizable cycloacetal compound 20% | 14 | 27 | 45 | 16 |
| unsaturated polyester (A)60% polymerizable cycloacetal compound 40% | 13 | 23 | 39 | 27 |
| unsaturated polyester (A)40% polymerizable cycloacetal compound 60% | 11 | 19 | 30 | 38 |
| styrene 10% polymerizable cycloacetal compound 90% | 28 | 37 | 50 | 53 |

EXAMPLE 6

Polymethylmethacrylate for an acrylic lacquer having a molecular weight of about 25,000 was dissolved in styrene to form a solution having 30 percent of solid content.

The above prepared styrene solution was mixed with 100 weight parts of the polymerizable cycloacetal compound of this invention in various ratios, and the resultant composition was tested in respect of an adhesive strength (shear strength) between steel plates as well as film formability of paint coating. As seem from Tables 2 and 3, the compositions of this invention proved to be excellent as adhesives or paints.

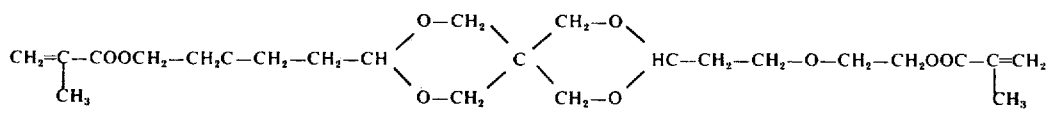

Table 2

| Composition of resin | | | adhesive strength after 48 hours (kg/cm²) |
|---|---|---|---|
| polymerizable cycloacetal compound | 100 | wt parts | |
| benzoyl peroxide | 1 | " | 116 – 130 |
| dimethyl aniline | 0.1 | " | |

Table 2-continued

| Composition of resin | | | adhesive strength after 48 hours (kg/cm²) |
|---|---|---|---|
| polymerizable cycloacetal compound | 100 | wt parts | |
| styrene solution of polymethyl-methacrylate | 10 | " | 150 – 163 |
| bynzoyl peroxide | 1.1 | " | |
| dimethyl aniline | 0.1 | " | |
| polymerizable cycloacetal compound | 100 | wt parts | |
| styrene solution of polymethyl-methacrylate | 20 | " | 161 – 184 |
| benzoyl peroxide | 1.2 | " | |
| dimethylaniline | 0.1 | " | |
| polymerizable cycloacetal compound | 100 | wt parts | |
| styrene solution of polymethyl-methacrylate | 30 | " | 204 – 247 |
| benzoyl peroxide | 1.3 | " | |
| dimethyl aniline | 0.1 | " | |

Table 3

| Composition of resin | | | state of film surface | Sword hardness after 48 hours |
|---|---|---|---|---|
| polymerizable cycloacetal compound | 90 | wt parts | partly orange-peel like lusterless surface | 53 |
| styrene | 10 | " | | |
| methylethyl ketone peroxide | 1.5 | " | | |
| cobalt naphthenate (6% Co) | 0.8 | " | | |
| polymerizable cycloacetal compound | 90 | wt parts | smooth and lustrous surface | 49 |
| styrene | 10 | " | | |
| styrene solution of polymethyl-methacrylate | 10 | " | | |
| methylethyl keton peroxide | 1.5 | " | | |
| cobalt naphthenate | 0.8 | | | |
| polymerizable cycloacetal compound | 90 | wt parts | smooth and lustrous surface | 55 |
| styrene | 10 | " | | |
| styrene solution of polymethyl-methacrylate | 20 | " | | |
| methylethyl ketone peroxide | 1.5 | " | | |
| cobalt naphthenate | 0.8 | | | |

The polymerizable cycloacetal compound of this invention may be used in connection with the other thermoplastic polymers such as vinyl copolymer, polystyrene, polyvinylmethylether and the like in the same manner as used in the preceding example.

EXAMPLE 7

1 weight part of benzoin methylether was dissolved in 100 weight parts of the polymerizable cycloacetal compound of this invention, and to the resultant mixture was added 10 weight parts of 30% styrene solution of polyvinyl acetate. The resultant composition was coated by a knife coater on a steel plate as used in Example 5 so as to make a thickness of a coated film 0.2 mm. This coated film was placed under a mercury lamp positioned at 10 cm apart from the coated film. The film was cured by 1–2 seconds' exposure to ultraviolet rays, and the pencil hardness of the cured surface reached 4 H after 5 seconds' exposure. Thus, resinous composition of this invention proved to be useful for a paint to be cured by ultraviolet rays.

EXAMPLE 8

90 weight parts of the polymerizable cycloacetal compound of this invention and 10 weight parts of styrene were mixed, and coated on a steel plate as used in Example 5 so as to make the thickness of a coated film 0.1 mm. The coated film was cured at a dosage of 3 mega-rad by a van de Graaf type electron beam radiation apparatus to form a cured film having a pencil hardness of 3–4 H.

100 weight parts of the polymerizable cycloacetal compound of this invention, 3 weight parts of phthalocyanine green, 20 weight parts of talc, 5 weight parts of titanium white and 20 weight parts of styrene were mixed by a roller, and the mixture was coated on a steel plate in the same manner as above. The coated film was cured by irradiating with an electron beam dosage of 3 megarads to form a colored cured film having a pencil hardness of 4 H.

EXAMPLE 9

Preparation of vinylester

Epoxy resin "Epikote 834" having an epoxy equivalent of 260 (made by Shell Co., Ltd.) 520 weight parts, acrylic acid 140 weight parts, hydroquinone (polymerization inhibitor) 0.14 weight part and diethylamine hydrochoric acid salt 2.5 weight parts were reacted at 125°C for 180 minutes to produce a vinyl ester resin having an acid value of 6.0.

The thus obtained vinyl ester resin was mixed with polymerizable cycloacetal compound as prepared in Example 2 in a weight ratio of vinyl ester 60 to cycloacetal compound 40, and the resultant mixture was coated on a steel plate to form a film having a thickness of 0.1 mm. The coated film was cured by irradiating with an electron beam dosage of 3 megarad beam to form a cured film having a pencil hardness of 4 H, and the adhesion to the steel plate was excellent.

What we claim is that:

1. A polymerizable cycloacetal composition, prepared by reacting 1 equivalent of (I) diallylidenepentaerythritol with 0.8–2.0 equivalents of (II) polyhydric alcohol-unsaturated monocarboxylic acid ester having one alcoholic hydroxyl group and at least one substituent selected from methacrylyl, acrylyl and crotonyl groups, with or without a solvent, in the presence of a free radical polymerization inhibitor and an addition reaction catalyst.

2. A polymerizable cycloacetal composition according to claim 1, wherein said polyhydric alcohol-unsaturated monocarboxylic acid ester (II) is selected from the group consisting of hydroxyethyl methacrylate, hydroxypropylmethacrylate, hydroxyethylacrylate, hydroxypropylacrylate, hydroxyethylcrotonate, hydroxypropylcrotonate, trimethylolpropanedimethacrylate, trimethylolpropanediacrylate, trimethylolethanedimethacrylate, trimethylolethanediacrylate and glycerinedimethacrylate.

* * * * *